United States Patent [19]
Artsi et al.

[11] Patent Number: 5,515,862
[45] Date of Patent: May 14, 1996

[54] FEMALE CONDOM

[75] Inventors: Elie Artsi, Yasmin Street 14, Carmei Yosef; Jacques Daniel, Rechovot, both of Israel

[73] Assignee: Elie Artsi, Cazmei Yosef, Israel

[21] Appl. No.: 348,117

[22] Filed: Nov. 28, 1994

[51] Int. Cl.⁶ .................... A61F 6/06; A61F 6/02
[52] U.S. Cl. .............. 128/830; 128/842; 128/844
[58] Field of Search .................. 128/842, 844, 128/916, 830–841; 604/330, 347–353

[56] References Cited

U.S. PATENT DOCUMENTS

| | | | |
|---|---|---|---|
| 3,130,721 | 4/1964 | Young | 128/844 |
| 4,664,104 | 5/1987 | Jaicks | 604/353 |
| 4,840,624 | 6/1989 | Lee | 604/349 |
| 4,981,147 | 1/1991 | Barnett | 128/842 |
| 5,069,228 | 12/1991 | Sorkin | 128/844 |
| 5,137,032 | 8/1992 | Harmon | 128/844 |
| 5,209,241 | 5/1993 | Hardy | 128/844 |
| 5,269,320 | 12/1993 | Hunnicutt | 128/830 |

*Primary Examiner*—Michael A. Brown
*Attorney, Agent, or Firm*—Mark M. Friedman

[57] ABSTRACT

A condom for use by a female user has a flexible tube for insertion into the vagina, the tube having a sealed end and an open end, a shield sealingly attached to or integrally formed with the open end, and an adhesive applied to a portion of the shield for detachably attaching the condom to the female user. The shield has a number of regions which together form a continuous, seamless surface surrounding the open end of the tube. These regions include a first region for covering the pubic region and part of the lower abdomen, a second region for substantially covering the right groin, a third region for substantially covering the left groin, a fourth region for covering part of the right inner thigh, a fifth region for covering part of the left inner thigh, and a sixth region for covering the perineum and the anus. One or more semi-rigid ring may be deployed along the tube. The adhesive is a perspiration resistant, hypo-allergenic skin glue.

4 Claims, 4 Drawing Sheets

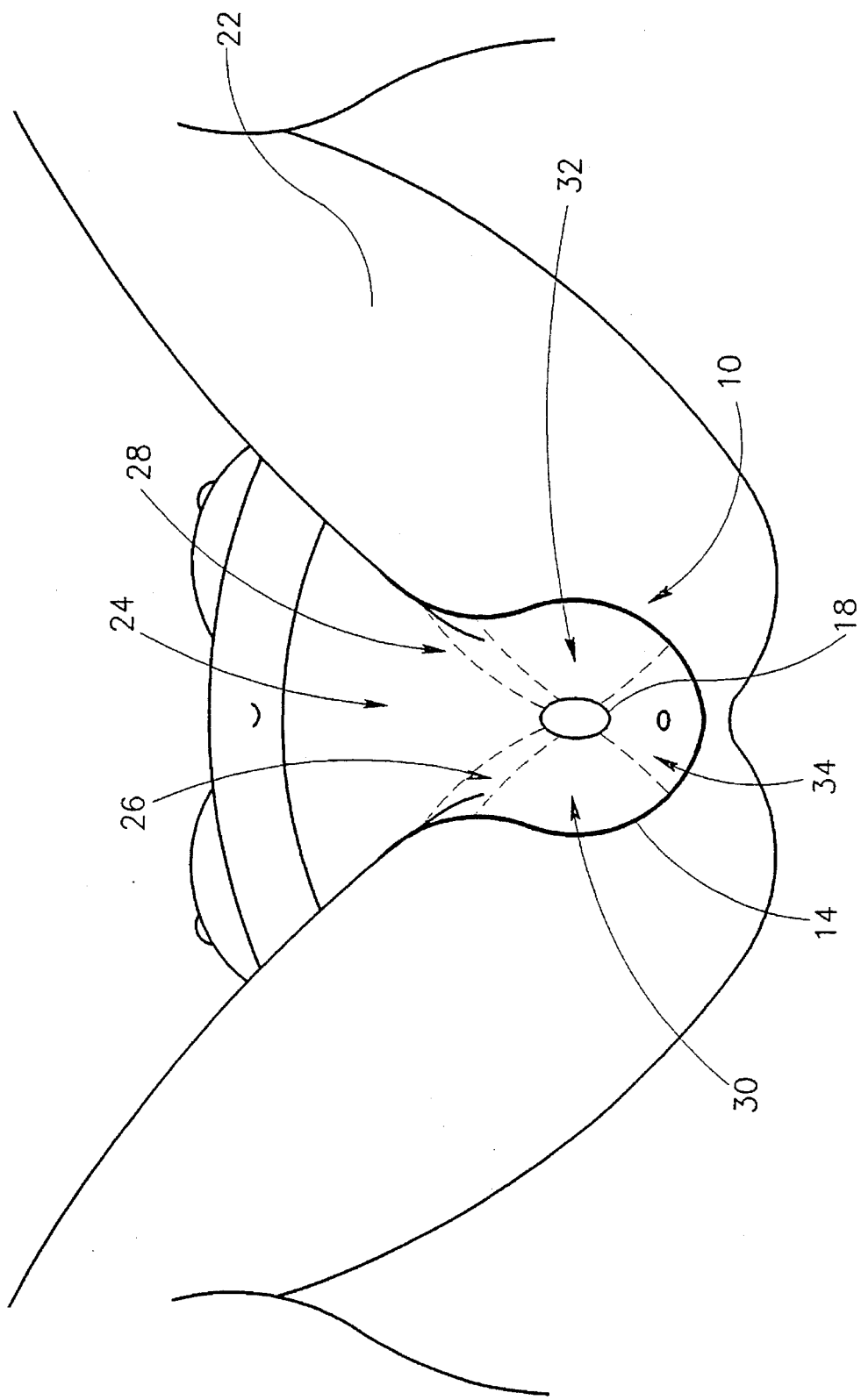

FEMALE CONDOM

FIELD AND BACKGROUND OF THE INVENTION

The present invention relates to barrier methods of contraception and protection from sexually transmitted diseases, in general. In particular, it concerns female condoms having an extended shield protecting the area surrounding the genitalia.

It is well known to use a physical barrier to prevent the release of sperm into the vagina during intercourse as a means of contraception. The most familiar barrier method of contraception is the use of a male condom. However, the male condom is far from ideal, having at least three major shortcomings: first, it has a failure rate generally estimated to be around 5 percent; second, it puts the majority of responsibility for contraception on the male partner (who, not himself being at risk of becoming pregnant, is often less conscientious); and third, since the condom must be placed over the erect penis before intercourse, it disturbs the spontaneity of relations.

Barrier methods of contraception have additional importance for the protection they offer against sexually transmitted diseases such as AIDS and other sexually transmitted viral, fungal, and bacterial infections. However, protection of the genital organs alone is often insufficient to prevent infection. Small, often inapparent, cracks and breaks in the skin are common in the skin surrounding the genitals, such as the inner thighs, the pubis, and in particular on the perineum and around the anus. The anus itself also presents an absorptive surface. When infected body fluids fall on these areas during or after intercourse, these cracks allow passage of infectious matter into the body.

Many attempts have been made to develop a female condom, but none has yet provided reliable contraception and effective protection from sexually transmitted diseases. U.S. Pat. No. 5,094,250 to Hessel describes a device, having a flexible tube with an open end and a closed end, a first ring for positioning the closed end of the device at the bottom of the vagina, and a second ring for preventing the open end of the tube from entering the vagina. This device, besides being difficult to keep in place during intercourse, does not protect against seepage around the second ring. It also fails to give protection against diseases transmitted by body fluids contacting the perineum or anal region.

U.S. Pat. No. 5,269,320 to Hunnicutt describes a female condom with a flange shaped shield retained in place by adhesive. The shield described, having a general triangular shape with a height of about 11 cm. and a maximum width of about 7 cm., cannot adhere efficiently to the skin surrounding the vulva because of the presence of the tuff of hair in this region. In one embodiment, the shield is included in a rubber crotch section of a panty, but even here the regions lateral to the vulva are not sufficiently covered by this device to safely provide prophylactic and contraceptive functions. Furthermore, no provisions are described to prevent seepage under the rubber crotch section.

In an attempt to address the aforementioned problems, U.S. Pat. No. 4,898,184 to Skurkovich et al. describes a female condom having a number of shield portions connected to a genital portion. FIGS. 1 and 2 show the Skurkovich device, in which their numbering system has been preserved and is used here in parentheses. According to their description, the female condom has an upper portion or apron (20) covering the lower abdomen and pubic area, a vaginal portion (22) and thigh portions (24) and (26). Thin belt portions (28), (30), (32) and (34) are integrally connected to the apron and thigh portions for attachment. Alternatively, the various portions may be attached to the skin by a narrow strip of glue-like material. FIG. 1 shows clearly that thigh portion (24) covers only the front of the thighs, leaving the rear of the inner thighs, part of the perineum and the anal area exposed. FIG. 2, (in which the triangular shape is somewhat enigmatic in its relation to thigh portions (24) and (26), and vaginal portion (22) seems to have vanished) shows clearly that upper portion (20) stops short of straps (30), (34), and therefore fails to give protection to the bottom of the groin and the front of the inner thigh. The weak glue, such as the 3M yellow paper glue, mentioned as an alternative method of attachment would be insufficient to hold the device in place without the straps. No provisions are described to prevent seepage of body fluids under the various portions of the device.

U.S. Pat. No. 5,069,228 describes a male condom with a small shield attached to the user by a peripheral ring of adhesive. The adhesive described is a copolymer of an acrylic ester and acrylic acid, which is a water resistant glue, painlessly removable from the skin. However, the device described is ineffective, the ring of adhesive being unable to adhere to the pubic hair on which it is located.

There is therefore a need for female condoms providing more reliable contraception, and improved protection from diseases transmitted through the skin surrounding the genital region.

SUMMARY OF THE INVENTION

The present invention is of female condoms with an extended shield part for protecting the area surrounding the genitalia.

Hence, there is provided according to the teachings of the present invention, a condom for use by a female user, the condom comprising: (a) a flexible tube for insertion into the vagina of the female user, the tube having a sealed end and an open end; (b) a shield sealingly attached to or integrally formed with the open end, the shield having a number of regions which together form a continuous, seamless surface surrounding the open end, the number of regions including: (i) a first region deployable to cover the pubic region and part of the lower abdomen of the female user, (ii) a second region deployable to substantially cover the right groin of the female user, (iii) a third region deployable to substantially cover the left groin of the female user, (iv) a fourth region deployable to cover part of the right inner thigh of the female user, (v) a fifth region deployable to cover part of the left inner thigh of the female user, and (vi) a sixth region deployable to cover the perineum and the anus of the female user; and (c) an adhesive applied to a portion of the shield for detachably attaching the condom to the female user.

According to a further feature of the present invention there is also provided a semi-rigid ring deployed along the tube proximate to the sealed end for positioning and maintaining the sealed end within the vagina of the female user.

According to a further feature of the present invention there is also provided at least one semi-rigid ring deployed along the tube at an intermediate position between the sealed end and the open end.

According to a further feature of the present invention the shield has an outer edge, the adhesive being applied substantially close to the outer edge so as to lie beyond the pubic hair line of the female user when the condom is worn by the female user.

According to a further feature of the present invention the portion surrounds the open end such that the adhesive seals between the shield and the skin of the female user to resist the passage of fluids.

According to a further feature of the present invention the adhesive is resistant to perspiration.

According to a further feature of the present invention the adhesive is hypo-allergenic.

There is also provided according to the teachings of the present invention, a condom for use by a female user, the condom comprising: (a) flexible tube for insertion into the vagina of the female user, the tube having a sealed end and an open end; (b) a shield sealingly attached to or integrally formed with the open end, the shield having a number of regions which together form a continuous, seamless surface surrounding the open end, the number of regions including: (i) a first region deployable to cover the pubic region and part of the lower abdomen of the female user, (ii) a second region deployable to substantially cover the right groin of the female user, (iii) a third region deployable to substantially cover the left groin of the female user, (iv) a fourth region deployable to cover part of the right inner thigh of the female user, (v) a fifth region deployable to cover part of the left inner thigh of the female user, and (vi) a sixth region deployable to cover the perineum and the anus of the female user; and (c) attachment means for detachably attaching the condom to the female user.

According to a further feature of the present invention there is also provided a semi-rigid ring deployed along the tube substantially proximate to the sealed end for positioning and maintaining the sealed end within the vagina of the female user.

According to a further feature of the present invention there is also provided at least one semi-rigid ring deployed along the tube at an intermediate position between the sealed end and the open end.

According to a further feature of the present invention the attachment means includes a plurality of straps attached to or integrally formed with the shield.

According to a further feature of the present invention the attachment means includes an adhesive applied to a portion of the shield.

According to a further feature of the present invention the shield has an outer edge, the adhesive being applied substantially close to the outer edge so as to lie beyond the pubic hair line of the female user when the condom is used by the female user.

According to a further feature of the present invention the adhesive is resistant to perspiration.

According to a further feature of the present invention the adhesive is hypo-allergenic.

According to a further feature of the present invention there is also provided sealing means for sealing between the shield and the skin of the female user to resist the passage of fluids.

According to a further feature of the present invention the sealing means includes an adhesive applied to a portion of the shield substantially surrounding the open end.

BRIEF DESCRIPTION OF THE DRAWINGS

The invention is herein described, by way of example only, with reference to the accompanying drawings, wherein:

FIG. 5 is a perspective view of the female condom of FIG. 3 positioned for use on a female user;

DESCRIPTION OF THE PREFERRED EMBODIMENTS

Figure 2:
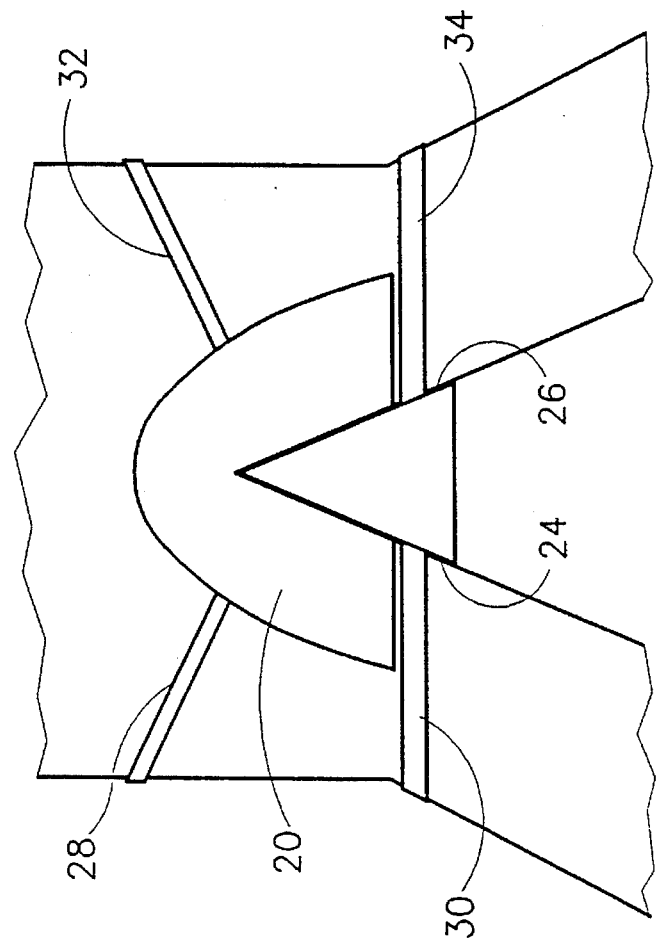
FIG. 2 is a front view of the female condom of FIG. 1.
Figure 1:
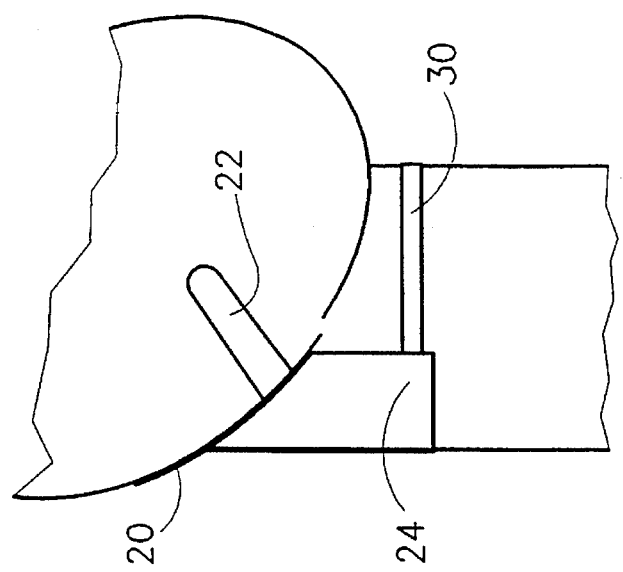
FIG. 1 is a side view of a female condom according to Skurkovich et al.

The present invention is of female condoms with an extended shield part for protecting the area surrounding the genitalia.

The principles and operation of female condoms according to the present invention may be better understood with reference to the drawings and the accompanying description.

Referring now to the drawings, FIGS. 3 to 7 illustrate the construction and use of a preferred embodiment of a female condom, constructed and operative according to the teachings of the present invention. This female condom is easy to wear, is well adapted to the anatomical and physiological characteristics of the genital region, and gives full protection without significantly interfering with the quality of the sexual intercourse. It is also simple to manufacture. The female condom is effective when used alone. Alternatively, it can be used in addition to a male condom, thereby reducing the risks of conception and of sexual transmission of disease to extremely low levels. An additional benefit of the presented device is to make sexual intercourse easier during menstrual periods, or in case of vaginal dryness or of irritation of the vaginal mucosa.

Figure 4:
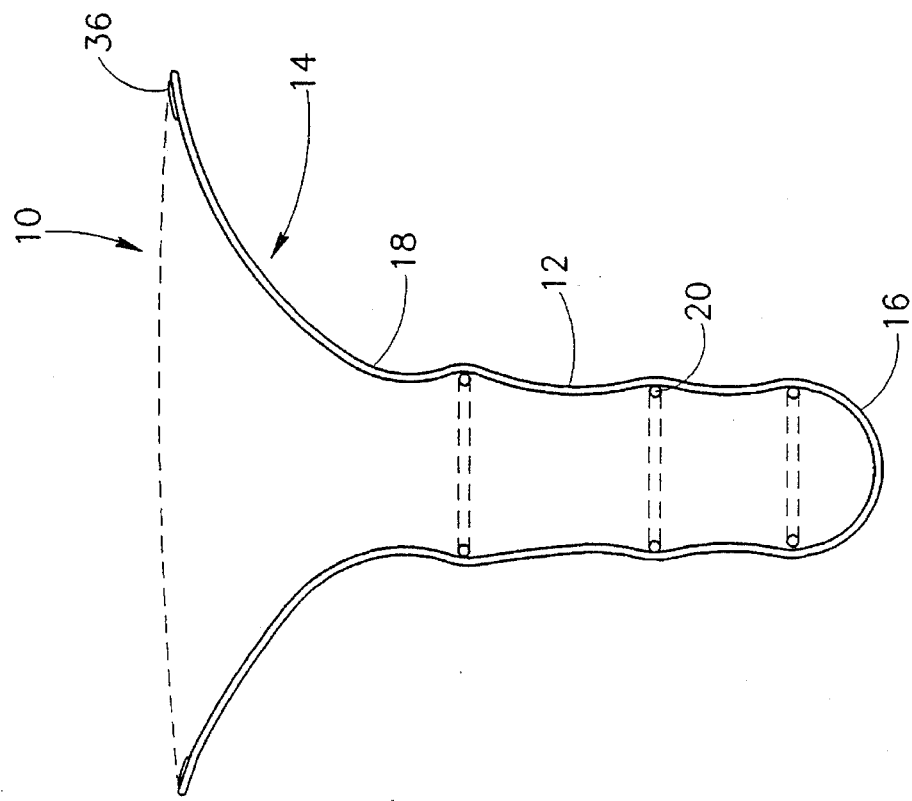
FIG. 4 is a cross-sectional view of the female condom of FIG. 3.
Figure 3:
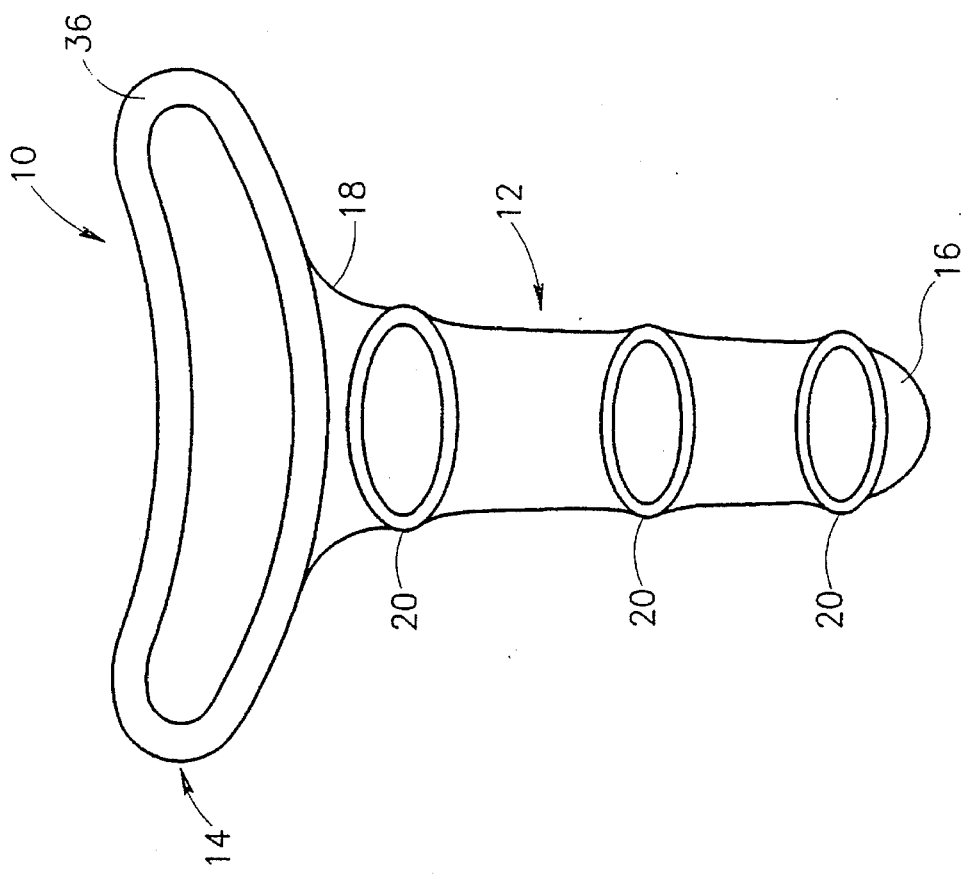
FIG. 3 is a perspective view of a female condom constructed and operative according to the teachings of the present invention.

FIGS. 3 and 4 show a female condom, generally designated 10. Generally speaking, female condom 10 has a flexible tube 12 for inserting into the vagina of a female user, a shield 14 for protecting the area surrounding the genitalia of the female user and adhesive material for detachably attaching female condom 10 to the female user. Both tube 12 and shield 14 are made of a thin soft water-impermeable material, for instance latex or any other biologically acceptable thermoplastic material, but need not necessarily be made of the same material.

More specifically, tube 12 has a sealed end 16, an open end 18, and may have one or more semi-rigid rings 20 spaced along tube 12. Semi-rigid rings 20 serve to prevent it from collapsing radially. They also lodge against the muscular tissue of the vaginal passage, thereby preventing slipping of tube 12 along the length of the vagina during use. Alternatively, these functions may be performed by a separate collar-shaped or otherwise shaped spacer element which is positioned within tube 12 after condom 10 is in place. One of semi-rigid rings 20 or any other resilient insert may be associated with sealed end 16 in order to facilitate insertion and maintain sealed end 16 at the bottom of the vagina. Ring 20 used for this purpose is generally of smaller diameter than one used at an intermediate position along tube 12, thereby fitting against the cervix in a manner similar to a conventional diaphragm. Tube 12 is typically 15–20 centimeters long. The sides of tube 12 may have smooth surfaces or, alternatively, one or both of its surfaces may be textured in order to increase sexual pleasure. Tube 12 may be provided with a solid or liquid lubricant on one or both of its surfaces. Sealed end 16 may also contain an absorbent material, a spermicide or an antiseptic material.

Shield 14 is sealingly attached to or integrally formed with open end 18 (herein taken to mean the part of tube 12 proximal to open end 18) around the entire circumference of open end 18. The shape and dimensions of shield 14 may best appreciated with reference to FIG. 5 in which female condom 10 is shown deployed on a female user 22. Shield 14 has a first region 24, delineated between dashed lines, extending to cover the pubic region and part of the lower abdomen, a second region 26 extending to substantially cover the right groin, a third region 28 extending to substantially cover the left groin, a fourth region 30 extending to cover part of the right inner thigh, a fifth region 32 extending to cover a part of the left inner thigh and a sixth region 34 extending to cover the perineum and the anus. All of these regions are connected such that shield 14 forms a unitary, continuous, seamless surface over the region of the body including the aforementioned anatomical features. In order to cover the areas of the body mentioned, shield 14 extends asymmetrically from open end 18, first region 24 extending much more than sixth region 34. Typically, the width of shield 14, measured from its periphery to open end 18, is at least 5 cm. at its narrowest, increasing to a width of at least 15 cm. for first region 24.

The material used for shield 14 is flexible, enabling shield 14 to be produced in a somewhat simplified shape and then deformed to fit the features of the body. Thus in a simple embodiment, shield 14 may have a flattened conical form, this form enabling particularly easy production of female condom 10. In other embodiments, shield 14 may be constructed in any of a large number of shapes and forms, including a pyramidal form and planar forms of various shapes. In a preferred embodiment, shield 14 is of saddle-like or similar shape in order to better fit the shape and relief of the body region to which it is attached.

Preferably, the adhesive material is applied to the surface of shield 14 adjacent to the skin as a strip 36 near the outer edge of shield 14. Unlike the prior art references mentioned above, strip 36, located near the periphery of shield 14, lies outside the pubic hairline so that the adhesive adheres well to the skin. As will become clear below, it is preferable that strip 36 is applied to a contiguous area of shield 14 extending around shield 14 so as to surround open end 18. Strip 36 may be replaced by other configurations, with adhesive applied to the entirety of the inner surface of shield 14, or selected parts thereof, for example avoiding regions which contact particularly sensitive tissue such as the clitoral region.

The adhesive of strip 36 is a water-resistant skin glue, painlessly removable from the skin. It is particularly important that the adhesive is resistant both to perspiration and to other body fluids, so that its functions are not impaired during and after intercourse. Suitable adhesives include a copolymer of an acrylic ester and acrylic acid. The adhesive is preferably also hypo-allergenic, an example of which is the adhesive used in slow release medicated patches commercially available from Ciba-Geigy (Switzerland).

In a preferred embodiment, strips 36 perform two functions: firstly, strip 36 is effective to attach female condom 10 to female user 22; and secondly, strip 36, surrounding open end 18 as described, provides a continuous leak-proof seal between shield 14 and female user 22, thereby preventing seepage of body fluids under shield 14 from outside the protected area. Thus, condom 10 provides effective protection, not only for the genitalia themselves, but also for the entire region covered by shield 14, thereby preventing transmission of sexually transmitted diseases through breaks in the skin of that area.

Alternative or additional means may be provided for attaching condom 10 to female user 22. This may include adjustable or elasticated straps, strings for tying or adhesive strips attached to shield 14.

Figure 7:
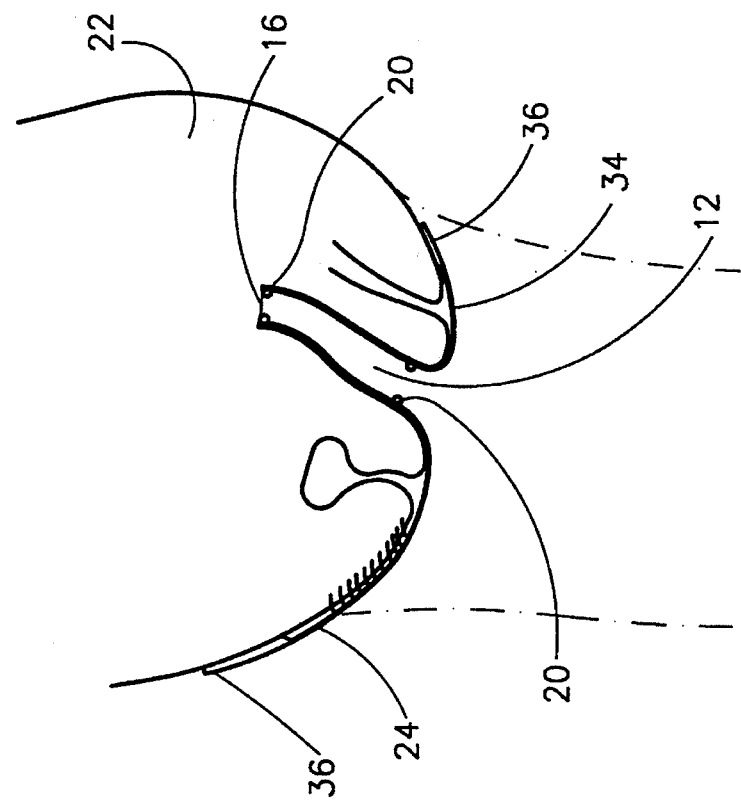
FIG. 7 is a cross-sectional view of the female condom of FIG. 3 positioned for use on a female user.
Figure 6:
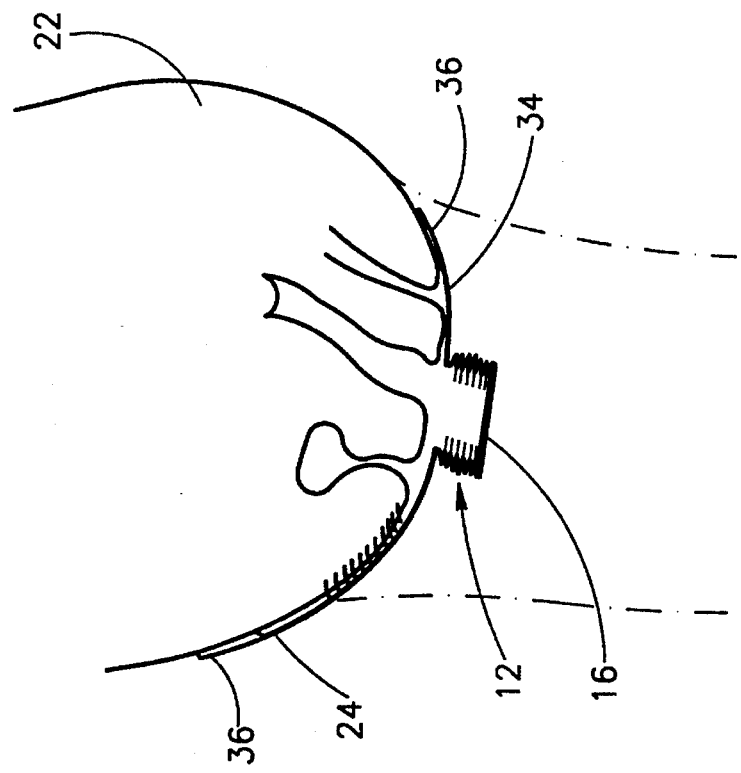
FIG. 6 is a cross-sectional view of the female condom of FIG. 3 positioned on a female user before insertion into the vagina.

Referring now to FIGS. 6 and 7, the use of female condom 10 will now be described. Female condom 10 may be packaged in a compact folded state for retail, preferably hermetically sealed in a foil packet. In this state, tube 12 is folded on itself in a manner similar to a concertina, and shield 14 is folded on to itself from each side. The adhesive of strip 36 is protected by a release paper.

At a convenient time prior to sexual relations, shield 14 is opened, the release paper is removed from strip 36 and shield 14 is positioned such that strip 36 adheres to the skin surrounding the vulva, on the pubis and lower abdomen beyond the tuff of hair, on the groins, at the inner regions of the thighs, on the perineum, anus, and inner regions of the buttocks. This position is illustrated in FIG. 6.

Inward pressure is then applied to folded tube 12 by a finger of the user or any other blunt object, thereby extending tube 12 and forcing sealed end 16 into position at the base of the vagina. Alternatively, the extension of tube 12 may be achieved by the insertion of the penis at the time of intercourse. In some embodiments, condom 10 is supplied with tube 12 inverted for packaging. In this case, tube 12 is reinverted by the process of insertion. Female condom 10 is then deployed ready for use as shown in FIG. 7. Once deployed, the flexibility of the material allows the female user full freedom of movement, without impairing the effectiveness of female condom 10. After use, female condom 10 may be pealed from the skin painlessly, and discarded.

It will be appreciated that the above descriptions are intended only to serve as examples, and that many other embodiments are possible within the spirit and the scope of the present invention.

What is claimed is:

1. A condom for use by a female user, the condom comprising:
   (a) a flexible tube for insertion into the vagina of the female user, said tube having a sealed end and an open end;
   (b) a shield sealingly attached to or integrally formed with said open end, said shield having a number of regions which together form a continuous, seamless surface surrounding said open end, said surface having a continuous outer edge, said number of regions including:
   (i) a first region deployable to cover the pubic region and part of the lower abdomen of the female user,
   (ii) a second region deployable to substantially cover the right groin of the female user, (iii) a third region deployable to substantially cover the left groin of the female user,
(iv) a fourth region deployable to cover part of the fight inner thigh of the female user,
(v) a fifth region deployable to cover part of the left inner thigh of the female user, and
(vi) a sixth region deployable to cover the perineum and the anus of the female user; and (c) an adhesive applied substantially close to, and around the entirety of said outer edge so as to lie beyond the pubic hair line of the female user, said adhesive forming a seal between said shield and the skin of the female user to resist the passage of fluids.

2. A condom as in claim 1, further comprising a plurality of semi-rigid rings deployed along a majority of the length of said tube.

3. A condom as in claim 1, wherein said adhesive is resistant to perspiration.

4. A condom as in claim 1, wherein said adhesive is hypoallergenic.

* * * * *